(12) United States Patent
Rohde et al.

(10) Patent No.: US 6,890,511 B2
(45) Date of Patent: May 10, 2005

(54) CRYSTALLINE ALUMINOSILICATE ZEOLITIC COMPOSITION: UZM-15

(75) Inventors: Lisa M. Rohde, Chicago, IL (US); Gregory J. Lewis, Mount Prospect, IL (US); Stephen T. Wilson, Libertyville, IL (US); Deng-Yang Jan, Elk Grove Village, IL (US); R. Lyle Patton, Rolling Meadows, IL (US); Susan C. Koster, Carpentersville, IL (US); Jaime G. Moscoso, Mount Prospect, IL (US); Mark A. Miller, Niles, IL (US); Michael G. Gatter, Elk Grove Village, IL (US)

(73) Assignee: UOP LLC, Des Plaines, IL (US)

( * ) Notice: Subject to any disclaimer, the term of this patent is extended or adjusted under 35 U.S.C. 154(b) by 43 days.

(21) Appl. No.: 10/395,399

(22) Filed: Mar. 21, 2003

(65) Prior Publication Data

US 2004/0186337 A1 Sep. 23, 2004

(51) Int. Cl.$^7$ .............................................. C01B 39/48
(52) U.S. Cl. ....................... 423/705; 423/708; 423/713; 423/718; 208/46
(58) Field of Search ............................... 423/705, 708, 423/718, 713

(56) References Cited

U.S. PATENT DOCUMENTS

| | | | |
|---|---|---|---|
| 4,172,856 A | 10/1979 | Spencer et al. | 585/640 |
| 4,191,709 A | 3/1980 | Parker et al. | 260/585 R |
| 4,197,186 A | 4/1980 | Short et al. | 208/120 |
| 4,205,012 A | 5/1980 | Parker et al. | 260/583 |
| 4,209,498 A | 6/1980 | Whittam | 423/328 |
| 4,241,036 A * | 12/1980 | Flanigen et al. | 502/62 |
| 4,578,259 A * | 3/1986 | Morimoto et al. | 423/703 |
| 4,689,207 A | 8/1987 | Zones | 423/332 |
| 4,698,217 A * | 10/1987 | Valyocsik | 423/706 |
| 4,873,067 A * | 10/1989 | Valyocsik et al. | 423/279 |
| 5,190,736 A * | 3/1993 | Hellring et al. | 423/706 |
| 5,397,560 A * | 3/1995 | Millar et al. | 423/700 |
| 6,077,498 A * | 6/2000 | Diaz Cabanas et al. | 423/702 |

FOREIGN PATENT DOCUMENTS

| | | |
|---|---|---|
| GB | 1563346 | 11/1976 |
| GB | 2006262 | 10/1978 |
| GB | 2006818 | 10/1978 |
| GB | 2013660 A | 1/1979 |
| GB | 2042490 | 2/1980 |
| GB | 2052554 A | 5/1980 |

* cited by examiner

*Primary Examiner*—David Sample
(74) *Attorney, Agent, or Firm*—John G. Tolomei; Frank S. Molinaro

(57) ABSTRACT

An aluminosilicate zeolite and substituted versions designated UZM-15 have been synthesized. These zeolites are prepared using an organoammonium cation as a template in which at least one organic group has at least 2 carbon atoms. An example of such a cation is diethyldimethylammonium cation. The template can optionally comprise other organoammonium cations, alkali metals and alkaline earth metals. These UZM-15 materials can be dealuminated by various processes to provide UZM-15HS compositions. Both the UZM-15 and UZM-15HS compositions are useful as catalysts or catalyst supports in various process such as the conversion of cyclic hydrocarbons to non-cyclic hydrocarbons and olefin oligomerization.

23 Claims, No Drawings

CRYSTALLINE ALUMINOSILICATE ZEOLITIC COMPOSITION: UZM-15

FIELD OF THE INVENTION

This invention relates to aluminosilicate zeolites designated UZM-15 and UZM-15HS a method of preparing the zeolites and uses thereof. The UZM-15 and UZM-15HS are useful in various hydrocarbon reactions such as the conversion of cyclic hydrocarbons to non-cyclic hydrocarbons, i.e. ring opening reactions.

BACKGROUND OF THE INVENTION

Zeolites are crystalline aluminosilicate compositions which are microporous and which are formed from corner sharing $AlO_2$ and $SiO_2$ tetrahedra. Numerous zeolites, both naturally occurring and synthetically prepared are used in various industrial processes. Synthetic zeolites are prepared via hydrothermal synthesis employing suitable sources of Si, Al, as well as structure directing agents such as alkali metals, alkaline earth metals, amines, or organoammonium cations. The structure directing agents reside in the pores of the zeolite and are largely responsible for the particular structure that is ultimately formed. These species balance the framework charge associated with aluminum and can also serve as space fillers. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure. Zeolites can be used as catalysts for hydrocarbon conversions, which can take place on outside surfaces as well as on internal surfaces within the pore.

U.S. Pat. No. 4,209,498 discloses an aluminosilicate zeolite designated as FU-1 along with a method of preparing the zeolite and uses for the zeolite. The '498 patent states that FU-1 is prepared using a "methylated quaternary ammonium" cation along with an alkali metal. It is further stated by the patentees that the FU-1 zeolite has a Si/Al ratio greater than 2.5 and can be used for xylene isomerization.

An all-silica version of FU-1 was reported in U.S. Pat. No. 4,689,207. The synthesis employs the layered silicate magadiite and the Na/ethyltrimethylammonium (ETMA) template system. The solid product was identified as containing 20% FU-1 by x-ray analysis.

A number of applications have been identified for the FU-1 zeolite. Besides the xylene isomerization mentioned above and disclosed in GB1563346, the conversion of alkylbenzenes, such as xylenes and ethylbenzene is described in GB2052554A, GB2006818, GB2042490, and GB2006262. U.S. Pat. No. 4,172,856 describes the use of FU-1 to make olefins from methanol or dimethylether as preferred feedstocks while U.S. Pat. Nos. 4,191,709, 4,205,012, and GB2013660A describe the synthesis of amines from alcohols using a FU-1 based catalyst. Finally, FU-1 based catalysts have been described for the cracking of heavy fractions to naphtha-type products in U.S. Pat. No. 4,197,186.

Applicants have prepared a family of zeolites, designated UZM-15, which have an x-ray diffraction pattern similar to but distinct from that of FU-1 and is different in other characteristics. One difference is that the as-synthesized UZM-15 contains at least one quaternary organoammonium cation template where at least one of the organic groups has at least two carbon atoms. Preferred templates are selected from ETMA, DEDMA, TMBA, PEDMA and optionally alkali metals, alkaline earth metals and/or other organoammonium cations. The Si/Al ratio of the UZM-15 zeolites ranges from about 7 to about 50 and the aluminum can be replaced by other metals such as gallium or iron.

Applicants have also prepared dealuminated versions of UZM-15 designated UZM-15HS. The UZM-15HS materials have different properties from the starting UZM-15, including different ion-exchange capacities, acidity, and porosity.

SUMMARY OF THE INVENTION

This invention relates to a new family of zeolites, a process for preparing the zeolites and processes using the zeolites. Accordingly, one embodiment of the invention is a microporous crystalline zeolite having a composition in the as-synthesized form in terms of mole ratios of the elements given by:

$$M_m^{n+}R_r^{p+}Al_{(1-x)}E_xSi_yO_z \quad (1)$$

where M is at least one exchangeable cation selected from the group consisting of alkali and alkaline earth metals, "in" is the mole ratio of M to (Al+E) and varies from 0 to about 2.0, R is at least one first quaternary organomnmonium cation comprising at least one organic group which has at least 2 carbon atoms, and optionally a second organoammonium cation selected from the group consisting of quaternary ammonium ions, protonated amines, protonated diamines, protonated alkanolamines, diquaternaryammonium ions, quaternized alkanolamines and mixtures thereof, "r" is the mole ratio of R to (Al+E) and has a value of about 0.25 to about 5.0, E is an element selected from the group consisting of Ga, Fe, In, Cr, B, and mixtures thereof, "x" is the mole fraction of E and varies from 0 to 1.0, "n" is the weighted average valence of M and has a value of about 1 to about 2, "p" is the weighted average valence of R and has a value of 1 to about 2, "y" is the mole ratio of Si to (Al+B) and varies from about 7 to about 50 and "z" is the mole ratio of O to Al+E) and has a value determined by the equation:

$$z=(m \cdot n+r \cdot p+3+4 \cdot y)/2;$$

the zeolite characterized in that it has an x-ray diffraction pattern having at least the d-spacings and relative intensities set forth in Table A.

TABLE A

| 2–θ | d (Å) | I/I₀ % |
|---|---|---|
| 8.35–9.30 | 10.58–9.75 | w–m |
| 12.30–13.30 | 7.19–6.65 | w–m |
| 16.60–17.20 | 5.34–5.15 | w–m |
| 19.00–19.80 | 4.67–4.48 | w–m |
| 20.80–22.30 | 4.27–3.98 | w |
| 23.55–23.95 | 3.77–3.71 | w–m |
| 24.03–24.47 | 3.70–3.63 | w–m |
| 25.50–26.25 | 3.49–3.39 | vs |
| 48.30–49.10 | 1.88–1.85 | w |

Another embodiment of the invention is a process for preparing the above-described zeolites which comprises forming a reaction mixture containing reactive sources of R, Al, Si and optionally E and/or M and heating the reaction mixture at a temperature of about 85° C. to about 225° C., the reaction mixture having a composition expressed in terms of mole ratios of the oxides of:

$$aM_{2/n}O:bR_{2/p}O:(1-c)Al_2O_3:cE_2O_3:dSiO_2:eH_2O$$

where "a" has a value of 0 to about 5.0, "b" has a value of about 1.5 to about 80, "c" has a value of 0 to about 1.0, "d"

has a value of 10 to about 100, and "e" has a value of about 100 to about 15000.

A further embodiment of the invention is a microporous crystalline zeolite having an empirical composition on an anhydrous basis in terms of mole ratios of the elements of:

$$M1_a^{n+}Al_{(1-x)}E_xSi_{y'}O_{z''}$$

where M1 is at least one exchangeable cation selected from the group consisting of alkali metals, alkaline earth metals, rare earth metals, ammonium ion, hydrogen ion and mixtures thereof, a is the mole ratio of M1 to (Al+E) and varies from 0.01 to about 50, E is an element selected from the group consisting of gallium, iron, boron, chromium, indium and mixtures thereof, x is the mole fraction of E and varies from 0 to about 1.0, n is the weighted average valence of M1 and has a value of about +1 to about +3, y' is the mole ratio of Si to (Al+E) and is greater than about 7 and z" is the mole ratio of O to (Al+E) and has a value determined by the equation:

$$z''=(a \cdot n+3+4 \cdot y')/2$$

the zeolite characterized in that it has an x-ray diffraction pattern having at least the d-spacings and relative intensities set forth in Table B.

TABLE B

| 2-θ | d (Å) | I/I$_o$ % |
|---|---|---|
| 8.75–10.30 | 10.12–8.60 | w–vs |
| 12.70–13.40 | 6.98–6.62 | m–s |
| 19.00–20.30 | 4.68–4.38 | w |
| 25.50–26.50 | 3.50–3.37 | m–vs |

Another embodiment of the invention is a process for preparing a modified microporous crystalline zeolite having an empirical composition on an anhydrous basis in terms of mole ratios of the elements of:

$$M1_a^{n+}Al_{(1-x)}E_xSi_{y'}O_z$$

where M1 is at least one exchangeable cation selected from the group consisting of alkali metals, alkaline earth metals, rare earth metals, ammonium ion, hydrogen ion and mixtures thereof, a is the mole ratio of M1 to (Al+E) and varies from about 0.01 to about 50, E is an element selected from the group consisting of gallium, iron, boron, chromium, indium and mixtures thereof, x is the mole fraction of E and varies from 0 to about 1.0, n is the weighted average valence of M1 and has a value of about +1 to about +3, y' is the mole ratio of Si to (Al+E) and is greater than about 7 and z" is the mole ratio of O to (Al+E) and has a value determined by the equation:

$$z''=(a \cdot n+3+4 \cdot y')/2$$

the zeolite characterized in that it has an x-ray diffraction pattern having at least the d-spacings and relative intensities of Table B, the process comprising treating a starting zeolite at treating conditions thereby removing at least a portion of the framework aluminum and optionally inserting silicon into the framework to provide the modified zeolite; the starting zeolite having an empirical formula on an anhydrous basis of:

$$M'_{m'}{}^{n+}R_{r'}^{p+}Al_{(1-x)}E_xSi_{y'}O_{z'}$$

where M' is an exchangeable cation selected from the group consisting of ammonium ion, hydrogen ion, alkali metals, alkaline earth metals, rare earth metals and mixtures thereof, n is the weighted average valence of M' and varies from +1 to about +3, m' is the mole ratio of M' to (Al+E) and varies from 0 to about 7.0, R is at least one first quaternary organoammonium cation comprising at least one organic group which has at least 2 carbon atoms, and optionally a second organoammonium cation selected from the group consisting of protonated amines, protonated diamines, protonated alkanolamines, quaternary ammonium ions, diquarternary ammonium ions, quaternized alkanolammonium ions and mixtures thereof, p is the average weighted valence of the organic cation and varies from about +1 to about +2, r' is the mole ratio of R to (Al+E) and varies from 0 to about 7.0, r'+m'>0, y' is the ratio of Si to (Al+E) and varies from about 7 to 50 and z' is the mole ratio of O to (Al+E) and has a value given by the equation:

$$z'=(m' \cdot n+r' \cdot p+3+4 \cdot y')/2.$$

Yet another embodiment of the invention is a hydrocarbon conversion process using any of the above-described zeolites. More specifically hydrocarbon conversion processes include hydroisomerization of normal paraffins to branched paraffins (especially mono-branched), oligomerization of light olefins and conversion of cyclic compounds to non-cyclic compounds, i.e. linear or branched compounds.

These and other objects and embodiments will become more apparent after the following detailed description of the invention.

DETAILED DESCRIPTION OF THE INVENTION

Applicants have synthesized a new family of zeolites designated UZM-15. In its as-synthesized form, the UZM-15 zeolite has a composition on an anhydrous basis that is represented by the formula:

$$M_m^{n+}R_{r}^{p+}Al_{(1-x)}E_xSi_yO_z \quad (1)$$

where M is an exchangeable cation and is selected from the group consisting of alkali and alkaline earth metals. Specific examples of the M cations include but are not limited to lithium, sodium, potassium, cesium, strontium, calcium, magnesium, barium and mixtures thereof. The value of "m" which is the mole ratio of M to (Al+E) varies from 0 to about 2.0. R is at least one first organoammonium cation comprising at least one organic group having at least two carbon atoms. Examples of these organoammonium cations include but are not limited to ethyltrimethylammonium (ETMA), diethyldimethylammonium (DEDMA), trimethylbutylammonium (TMBA), N,N,N,N',N'N'-hexamethyl-1,4 butanediammonium (DQ$_4$) and propylethyldimethylammonium (PEDMA). Optionally, R may be a mixture of at least one first organoammonium cation and second organoammonium cation selected from the group consisting of quaternary ammonium cations, protonated amines, protonated diamines, protonated alkanolamines, diquaternary ammonium cations, quaternized alkanolammonium cations and mixtures thereof. The value of "r" which is the mole ratio of R to (Al+E) varies from about 0.25 to about 5.0. The value of "n" which is the weighted average valence of M varies from +1 to about +2. The value of "p", which is the average weighted valence of the organic cation has a value from about +1 to about +2. E is an element which is present in the framework and is selected from the group consisting of gallium, iron, boron chromium, indium and mixtures thereof. The value of "x" which is the mole fraction of E varies from 0 to about 1.0. The ratio of silicon to (Al+E) is represented by "y" which varies from about 7 to about 50, while the mole ratio of O to (Al+E) is represented by "z" and has a value given by the equation:

$$z=(m \cdot n + r \cdot p + 3 + 4 \cdot y)/2.$$

When M is only one metal, then the weighted average valence is the valence of that one metal, i.e. +1 or +2. However, when more than one M metal is present, the total amount of:

$$M_m^{n+} = M_{m1}^{(n1)+} + M_{m2}^{(n2)+} + M_{m3}^{(n3)+} + \ldots$$

and the weighted average valence "n" is given by the equation:

$$n = \frac{m_1 \cdot n_1 + m_2 \cdot n_2 + m_3 \cdot n_3 + \ldots}{m_1 + m_2 + m_3 \ldots}$$

Similarly when only one R organic cation is present, the weighted average valence is the valence of the single R cation, i.e., +1 or +2. When more than one R cation is present, the total amount of R is given by the equation:

$$R_r^{p+} = R_{r1}^{(p1)+} + R_{r2}^{(p2)+} + R_{r3}^{(p3)+}$$

and the weighted average valence "p" is given by the equation:

$$p = \frac{p_1 \cdot r_1 + p_2 \cdot r_2 + p_3 \cdot r_3 + \ldots}{r_1 + r_2 + r_3 + \ldots}.$$

These aluminosilicate zeolites, are prepared by a hydrothermal crystallization of a reaction mixture prepared by combining reactive sources of R, aluminum, optionally E and/or M and silicon in aqueous media. Accordingly, the aluminum sources include, but are not limited to, aluminum alkoxides, precipitated alumina, aluminum hydroxide, aluminum salts and aluminum metal. Specific examples of aluminum alkoxides include, but are not limited to aluminum orthosec-butoxide, and aluminum orthoisopropoxide. Sources of silica include but are not limited to tetraethylorthosilicate, fumed silicas, precipitated silicas and colloidal silica. Sources of the M metals include but are not limited to the halide salts, nitrate salts, acetate salts, and hydroxides of the respective alkali or alkaline earth metals. Sources of the E elements include but are not limited to alkali borates, boric acid, precipitated gallium oxyhydroxide, gallium sulfate, ferric sulfate, ferric chloride, chromium chloride, chromium nitrate, indium chloride and indium nitrate. When R is a first organoammonium cation having at least one organic group with at least two carbon atoms, e.g. DEDMA, ETMA, TMBA, DQ$_4$ and PEDMA, the sources include but are not limited to the hydroxide, chloride, bromide, iodide, and fluoride compounds. R may also optionally be (in addition to the first organoammonium cation) a second organoammonium compound. In the case where R (second) is a quaternary ammonium cation or a quaternized alkanolammonium cation, the sources can be the hydroxide, chloride, bromide, iodide and fluoride compounds. Specific examples (either first or second cation) include without limitation ethyltrimethylammonium hydroxide (ETMAOH), diethyldimethylammonium hydroxide (DEDMAOH), propylethyldimethylammonium hydroxide (PEDMAOH), trimethylpropylammonium hydroxide, trimethylbutylammonium hydroxide (TMBAOH), tetraethylammonium hydroxide, hexamethonium bromide, tetramethylammonium chloride N,N,N,N',N',N'-hexamethyl 1,4 butanediammonium hydroxide, methyltriethylammonium hydroxide. The source of R may also be neutral amines, diamines, and alkanolamines. Specific examples are triethanolamine, triethylamine, and N,N,N',N' tetramethyl-1,6-hexanediamine. In a special case, a reagent in the form of an aluminosilicate stock solution may be used. These solutions consist of one or more organoammonium hydroxides and sources of silicon and aluminum that are processed to form a clear homogenous solution that is generally stored and used as a reagent. The reagent contains aluminosilicate species that typically don't show up in zeolite reaction mixtures derived directly from separate sources of silicon and aluminum. The reagent is generally alkali-free or contains alkali at impurity levels from the silicon, aluminum, and organoammonium hydroxide sources. One or more of these solutions may be used in a zeolite synthesis. In the case of substitution of Al by E, the corresponding metallosilicate solution may also be employed in a synthesis.

The reaction mixture containing reactive sources of the desired components can be described in terms of molar ratios of the oxides by the formula:

where "a" is the mole ratio of the oxide of M and has a value of 0 to about 5, "b" is the mole ratio of the oxide of R and has a value of about 1.5 to about 80, "d" is the mole ratio of silica and has a value of about 10 to about 100, "c" is the mole ratio of the oxide of E and has a value from 0 to about 1.0, and "e" is the mole ratio of water and has a value of about 100 to about 15000. The reaction mixture is now reacted at reaction conditions including a temperature of about 85° C. to about 225° C. and preferably from about 140° C. to about 175° C. for a period of about 12 hours to about 20 days and preferably for a time of about 2 days to about 10 days in a sealed reaction vessel under The crystalline zeolites are characterized by a three-dimensional framework structure of at least SiO$_2$ and AlO$_2$ tetrahedral units. These zeolites are further characterized by their x-ray diffraction pattern. The x-ray diffraction pattern has at least the diffraction lines with the d-spacings and relative intensities listed in Table A.

TABLE A

| 2–θ | d (Å) | I/I$_o$ % |
|---|---|---|
| 8.35–9.30 | 10.58–9.75 | w–m |
| 12.30–13.30 | 7.19–6.65 | w–m |
| 16.60–17.20 | 5.34–5.15 | w–m |
| 19.00–19.80 | 4.67–4.48 | w–m |
| 20.80–22.30 | 4.27–3.98 | w |
| 23.55–23.95 | 3.77–3.71 | w–m |
| 24.03–24.47 | 3.70–3.63 | w–m |
| 25.50–26.25 | 3.49–3.39 | vs |
| 48.3–49.10 | 1.88–1.85 | w |

As-synthesized, the zeolite will contain some of the exchangeable or charge balancing cations in its pores. These exchangeable cations can be exchanged for other cations, or in the case of organic cations, they can be removed by heating under controlled conditions. Ion exchange involves contacting the zeolites with a solution containing the desired cation (at molar excess) at exchange conditions. Exchange conditions include a temperature of about 15° C. to about 100° C. and a time of about 20 minutes to about 50 hours. Calcination conditions include a temperature of about 300° C. to about 600° C. for a time of about 2 to about 24 hours.

A special treatment for removing organic cations, which provides the ammonium form of the zeolite is ammonia calcination. Calcination in an ammonia atmosphere can decompose organic cations, presumably to a proton form that can be neutralized by ammonia to form the ammonium cation. The resulting ammonium form of the zeolite can be further ion-exchanged to any other desired form. Ammonia calcination conditions include treatment in the ammonia atmosphere at temperatures between about 250° C. and about 600° C. and more preferably between about 250° C. and about 450° C. for times of 10 minutes to 5 hours. Optionally, the treatments can be carried out in multiple steps within this temperature range such that the total time in the ammonia atmosphere does not exceed 5 hours. Above 500° C., the treatments should be brief, less than a half hour and more preferably on the order of 5–10 minutes. Extended calcination times above 500° C. can lead to unintended dealumination along with the desired ammonium ion-exchange and are unnecessarily harsh as most organoammonium templates easily decompose at lower temperatures.

The ion exchanged form of UZM-15 can be described by the empirical formula:

$$M'_{m'}{}^{n'+}R_{r'}{}^{p+}Al_{(1-x)}E_xSi_yO_{z'} \quad (2)$$

where R, x, y, and E are as described above and m' has a value from 0 to about 7.0, M' is a cation selected from the group consisting of alkali metals, alkaline earth metals, rare earth metals, hydrogen ion, ammonium ion, and mixtures thereof, n' is the weighted average valence of M' and varies from about 1 to about 3, r' has a value from 0 to about 7.0, r'+m'>0, and p is the weighted average valence of R and varies from about +1 to +2. The value of z' is given by the formula:

$$z'=(m'\cdot n'+r'\cdot p+3+4\cdot y)/2.$$

The UZM-15 zeolites represented by equation (2) can be further treated in order to remove aluminum and optionally inserting silicon thereby increasing the Si/Al ratio and thus modifying the acidity and ion exchange properties of the zeolites. These treatments include: a) contacting with a fluorosilicate solution or slurry; b) calcining or steaming followed by acid extraction or ion-exchange; c) acid extraction or d) any combination of these treatments in any order.

Fluorosilicate treatment is known in the art and is described in U.S. Pat. No. 6,200,463 B1, which cites U.S. Pat. No. 4,711,770 as describing a process for treating a zeolite with a fluorosilicate salt. Both patents are incorporated by reference in their entirety. General conditions for this treatment are contacting the zeolite with a solution containing a fluorosilicate salt such as ammonium fluorosilicate (AFS) at a temperature of about 20° C. to about 90° C.

The acids which can be used in carrying out acid extraction include without limitation mineral acids, carboxylic acids and mixtures thereof. Examples of these include sulfuric acid, nitric acid, ethylenediaminetetraacetic acid (EDTA), citric acid, oxalic acid, etc. The concentration of acid which can be used is not critical but is conveniently between about 1 wt. % to about 80 wt. % acid and preferably between 5 wt. % and 40 wt. % acid. Acid extraction conditions include a temperature of about 10° C. to about 100° C. for a time of about 10 minutes to about 24 hours. Once treated with the acid, the treated UZM-15 zeolite is isolated by means such as filtration, washed with deionized water and dried at ambient temperature up to about 100° C. The UZM-15 zeolites which have undergone one or more treatments whereby aluminum has been removed and optionally silicon has been inserted into the framework will hereinafter be referred to as UZM-15HS.

The extent of dealumination obtained from acid extraction depends on the cation form of the starting UZM-15 as well as the acid concentration and the time and temperature over which the extraction is conducted. For example, if organic cations are present in the starting UZM-15, the extent of dealumination will be slight compared to a UZM-15 in which the organic cations have been removed. This may be preferred if it is desired to have dealumination just at the surface of the UZM-15. As stated above, convenient ways of removing the organic cations include calcination, ammonia calcination, steaming and ion exchange. Calcination, ammonia calcination and ion exchange conditions are as set forth above. Steaming conditions include a temperature of about 400° C. to about 850° C. with from about 1% to about 100% steam for a time of about 10 minutes to about 48 hours and preferably a temperature of about 500° C. to about 600° C., steam concentration of about 5 to about 50% and a time of about 1 to about 2 hours.

It should be pointed out that both calcination and steaming treatments not only remove organic cations, but can also dealuminate the zeolite. Thus, alternate embodiments for dealumination include: a calcination treatment followed by acid extraction and steaming followed by acid extraction. A further embodiment for dealumination comprises calcining or steaming the starting UZM-15 zeolite followed by an ion-exchange treatment. Of course an acid extraction can be carried out concurrently with, before or after the ion exchange.

The ion exchange conditions are the same as set forth above, namely a temperature of about 15° C. to about 100° C. and a time of about 20 minutes to about 50 hours. Ion exchange can be carried out with a solution comprising a cation (M1') selected from the group consisting of alkali metals, alkaline earth metals, rare earth metals, hydrogen ion, ammonium ion, and mixtures thereof. By carrying out this ion exchange, the M1 cation is exchanged for a secondary or different M1' cation. In a preferred embodiment, the UZM-15HS composition after the steaming or calcining steps is contacted with an ion exchange solution comprising an ammonium salt. Examples of ammonium salts include but are not limited to ammonium nitrate, ammonium chloride, ammonium bromide, and ammonium acetate. The ammonium ion containing solution can optionally contain a mineral acid such as but not limited to nitric, hydrochloric, sulfuric and mixtures thereof. The concentration of the mineral acid is that amount necessary to give a ratio of $H^+$ to $NH_4^+$ of 0 to 1. This ammonium ion exchange aids in removing any debris present in the pores after the steaming and/or calcination treatments.

It is apparent from the foregoing that, with respect to effective process conditions, it is desirable that the integrity of the zeolite crystal structure be substantially maintained throughout the dealumination process, and that the zeolite retains at least 50%, preferably at least 70% and more preferably at least 90% of its original crystallinity. A convenient technique for assessing the crystallinity of the products relative to the crystallinity of the starting material is the comparison of the relative intensities of the d-spacing of their respective X-ray powder diffraction patterns. The sum of the peak intensities, in arbitrary units above the background, of the starting material is used as the standard and is compared with the corresponding peak intensities of the products. When, for example, the numerical sum of the peak heights of the molecular sieve product is 85 percent of the value of the sum of the peak intensities of the starting zeolite, then 85 percent of the crystallinity has been retained. In practice it is common to utilize only a portion of the peaks for this purpose, as for example, five or six of the strongest peaks. Other indications of the retention of crystallinity are surface area and adsorption capacity. These tests may be preferred when the substituted metal significantly changes, e.g., increases, the absorption of x-rays by the sample or when peaks experience substantial shifts such as in the dealumination process.

After having undergone any of the dealumination treatments as described above, the UZM-15HS is usually dried and can be used in various processes as discussed below. Applicants have found the properties of the UZM-15HS can be further modified by one or more additional treatment. These treatments include steaming, calcining or ion exchanging and can be carried out individually or in any combination. Some of these combinations include but are not limited to:

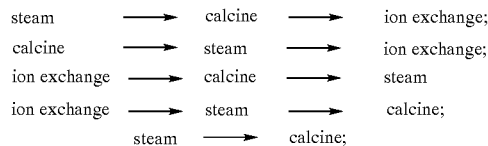

The dealumination treatment described above can be combined in any order to provide the zeolites of the invention although not necessarily with equivalent result. It should be pointed out that the particular sequence of treatments, e.g., AFS, acid extraction, steaming, calcining, etc., can be repeated as many times as necessary to obtain the desired properties. Of course one treatment can be repeated while not repeating other treatments, e.g., repeating the AFS two or more times before carrying out steaming or calcining; etc. Finally, the sequence and/or repetition of treatments will determine the properties of the final UZM-15HS composition.

The UZM-15HS as prepared above is described by the empirical formula on an anhydrous basis of $$M1_a^{n+}Al_{(1-x)}E_xSi_{y'}O_{z''} \quad (3)$$

where M1 is at least one exchangeable cation selected from the group consisting of alkali, alkaline earth metals, rare earth metals, ammonium ion, hydrogen ion and mixtures thereof, a is the mole ratio of M1 to (Al+E) and varies from about 0.01 to about 50, n is the weighted average valence of M1 and has a value of about +1 to about +3, E is an element selected from the group consisting of gallium, iron, boron, chromium, indium and mixtures thereof, x is the mole fraction of E and varies from 0 to 1.0, y' is the mole ratio of Si to (Al+E) and varies from greater than 7.0 to virtually pure silica and z" is the mole ratio of O to (Al+E) and has a value determined by the equation:

By virtually pure silica is meant that virtually all the aluminum and/or the E metals have been removed from the framework. It is well know that it is virtually impossible to remove all the aluminum and/or E metal. Numerically, a zeolite is virtually pure silica when y' has a value of at least 3,000, preferably 10,000 and most preferably 20,000. Thus, ranges for y' are from 7 to 3,000 preferably greater than 10 to about 3,000; 7.0 to 10,000 preferably greater than 10 to about 10,000 and 7.0 to 20,000 preferably greater than 10 to about 20,000.

In specifying the proportions of the zeolite starting material or adsorption properties of the zeolite product and the like herein, the "anhydrous state" of the zeolite will be intended unless otherwise stated. The term "anhydrous state" is employed herein to refer to a zeolite substantially devoid of both physically adsorbed and chemically adsorbed water.

The zeolites of this invention (both UZM-15 and UZM-15HS) are capable of separating mixtures of molecular species based on the molecular size (kinetic diameter) or on the degree of polarity of the molecular species. When the separation of molecular species is based on molecular size, separation is accomplished by the smaller molecular species entering the intracrystalline void space while excluding larger species. The kinetic diameters of various molecules such as oxygen, nitrogen, carbon dioxide, carbon monoxide are provided in D. W. Breck, *Zeolite Molecular Sieves*, John Wiley and Sons (1974) p. 636.

The crystalline microporous compositions of the present invention either as-synthesized or after modification can be used as catalysts or catalyst supports in hydrocarbon conversion processes. Hydrocarbon conversion processes are well known in the art and include ring-opening, cracking, hydrocracking, alkylation of both aromatics and isoparaffins, isomerization, polymerization, reforming, dewaxing, hydrogenation, dehydrogenation, transalkylation, dealkylation, hydration, dehydration, hydrotreating, hydrodenitrogenation, hydrodesulfurization, methanation and syngas shift process. Specific reaction conditions and the types of feeds which can be used in these processes are set forth in U.S. Pat. Nos. 4,310,440 and 4,440,871 which are incorporated by reference. A preferred hydrocarbon conversion process is ring-opening, whereby cyclic hydrocarbons are converted to non-cyclic hydrocarbons, i.e. linear or branched hydrocarbons. Other preferred processes include hydroisomerization of normal paraffins to branched paraffins and especially mono-branched paraffins and oligomerization of light olefins to higher molecular weight olefins.

Other reactions may be catalyzed by these crystalline microporous compositions, including base-catalyzed side chain alkylation of alkylaromatics, aldol-condensations, olefin double bond isomerization and isomerization of acetylenes, alcohol dehydrogenation, and olefin dimerization, oligomerization and conversion of alcohol to olefins. Suitably ion exchanged forms of these materials can catalyze the reduction of $NO_x$ to $N_2$ in automotive and industrial exhaust streams. Some of the reaction conditions and types of feeds that can be used in these processes are set forth in U.S. Pat. No. 5,015,796 and in H. Pines, THE CHEMISTRY OF CATALYTIC HYDROCARBON CONVERSIONS, Academic Press (1981) pp. 123–154 and references contained therein, which are incorporated by reference.

The X-ray patterns presented in the following examples (and tables above) were obtained using standard X-ray powder diffraction techniques. The radiation source was a high-intensity X-ray tube operated at 45 kV and 35 ma. The diffraction pattern from the copper K-alpha radiation was obtained by appropriate computer based techniques. Flat compressed powder samples were continuously scanned at 2° (2θ) per minute from 2° to 70° (2θ), or optionally from 3° to 40° (2θ) in 0.05° steps at 3° (2θ) per minute. Interplanar spacings (d) in Angstrom units were obtained from the position of the diffraction peaks expressed as 2θ where θ is the Bragg angle as observed from digitized data. Intensities were determined from the integrated area of diffraction peaks after subtracting background, "I$_o$" being the intensity of the strongest line or peak, and "I" being the intensity of each of the other peaks.

As will be understood by those skilled in the art, the determination of the parameter 2θ is subject to both human and mechanical error, which in combination can impose an uncertainty of about ±0.4 on each reported value of 2θ and up to ±0.5 on reported values for nanocrystalline materials. This uncertainty is, of course, also manifested in the reported values of the d-spacings, which are calculated from the θ values. This imprecision is general throughout the art and is not sufficient to preclude the differentiation of the present crystalline materials from each other and from the compositions of the prior art. In some of the X-ray patterns reported, the relative intensities of the d-spacings are indicated by the notations vs, s, m and w which represent very strong, strong, medium, and weak, respectively. In terms of 100 × I/I$_o$, the above designations are defined as w=0–15; m=15–60; s=60–80 and vs=80–100. In certain instances the purity of a synthesized product may be assessed with reference to its X-ray powder diffraction pattern. Thus, for example, if a sample is stated to be pure, it is intended only that the X-ray pattern of the sample is free of lines attributable to crystalline impurities, not that there are no amorphous materials present.

In order to more fully illustrate the invention, the following examples are set forth. It is to be understood that the examples are only by way of illustration and are not intended as an undue limitation on the broad scope of the invention as set forth in the appended claims.

EXAMPLE 1

Aluminum tri-sec-butoxide (95%), 46.32 g, was added to 626.31 g diethyldimethylammonium hydroxide (20%) and dissolved with vigorous stirring. To this mixture, 142.5 g precipitated silica, Ultrasil™ VNSP3 (85% SiO$_2$), was added with continuous stirring. In a separate beaker, 21.47 g TMACl (97%) and 5.22 g NaCl were dissolved in 58.18 g de-ionized H$_2$O. This solution was then added to the previous reaction mixture. The resulting mixture was homogenized for 20 min. The final reaction mixture was then distributed among several autoclaves including two 0.6 L stainless steel stirred autoclaves. The 0.6L autoclaves were heated to and held at 150° C., one for 120 hr and the other for 139 hr. The solids were then collected by centrifugation, washed with de-ionized water and dried at 950° C.

The products isolated from these 0.6L reactions exhibited an x-ray diffraction pattern with the characteristic lines for the zeolite designated UZM-15. Representative diffraction lines for the 139 hr product are listed in Table 1. Elemental analysis showed the composition of the same product to consist of the elemental mole ratios Si/Al=11.37, Na/Al=1.87, N/Al=2.02, and C/N=4.62. This material was calcined in a nitrogen atmosphere by ramping to 538° C., holding for 2 hr at 538° C., switching to an air atmosphere and holding at 538° C. for an additional 15 hr. Nitrogen adsorption measurements showed that the zeolite had a BET surface area of 332 m$^2$/g and a micropore volume of 0.10 cc/g.

TABLE 1

| 2–θ | d (Å) | I/I$_o$ % |
|---|---|---|
| 8.75 | 10.10 | m |
| 12.936 | 6.84 | m |
| 16.92 | 5.23 | w |
| 19.30 | 4.60 | m |
| 21.74 | 4.08 | w |
| 23.80 | 3.74 | m |
| 24.22 | 3.67 | m |
| 25.84 | 3.44 | vs |
| 48.62 | 1.87 | w |

An aluminosilicate stock solution was prepared in the following manner. Aluminum tri-sec-butoxide (95+%), 33.92 g, was added to 706.03 g ethyltrimethylammonium hydroxide (12.8%) with vigorous stirring. To this mixture, 255.22 g colloidal silica, (Ludox™ AS-40, 40% SiO$_2$) was added, followed by the addition of 4.84 g distilled water. The reaction mixture was homogenized for ½ hr with a high-speed mechanical stirrer, and then aged in a teflon bottle overnight at 98° C. After the aging step, the resulting aluminosilicate stock solution was analyzed and found to contain 4.91 wt. % Si and 0.48 wt. % Al.

A 46.24 g portion of the above aluminosilicate stock solution was weighed into a beaker. In a separate beaker, 0.48 g NaCl was dissolved in 3.27 g deionized H$_2$O. While stirring, the NaCl solution was then added to the previous reaction mixture. The resulting mixture was then stirred for 15 min. A 12.12 g portion of the final reaction mixture was transferred to a 23 mL Telfon-lined autoclave. The autoclave was then placed in an oven set at 150° C. and the mixture digested for 14 days at autogenous pressure. The solid was collected by centrifugation, washed and dried at 95° C.

The isolated product was identified as UZM-15 via x-ray powder diffraction analysis. Characteristic diffraction lines for the product are listed in Table 2. The product composition was determined by elemental analysis, which yielded the elemental mole ratios Si/Al=8.56, Na/Al=0.22, N/Al=0.97, and C/N=5.22.

TABLE 2

| 2–θ | d (Å) | I/I$_o$ % |
|---|---|---|
| 8.96 | 9.86 | w |
| 12.69 | 6.97 | w |
| 16.82 | 5.27 | w |
| 19.21 | 4.62 | m |
| 21.64 | 4.10 | w |
| 23.71 | 3.75 | w |
| 24.16 | 3.68 | w |
| 25.88 | 3.44 | vs |
| 48.58 | 1.87 | w |

EXAMPLE 3

A 46.04 g portion of the aluminosilicate stock solution prepared in Example 2 was weighed into a beaker. In a separate beaker, 0.46 g TMACl and 0.24 g NaCl was dissolved in 3.26 g de-ionized H$_2$O. This solution was then added to the aluminosilicate stock solution with vigorous mixing. The resulting mixture was homogenized for an additional 15 min before a 12.09 g portion was transferred to a 23 mL Telfon-lined autoclave. The autoclave was then placed in an oven set at 150° C. and digested for 14 days at autogenous pressure. The solid product was collected by centrifugation, washed with de-ionized water, and dried at 95° C.

The product was identified as UZM-15 by powder x-ray diffraction analysis. Diffraction lines characteristic of the product are listed in Table 3. Elemental analysis showed the product composition to consist of the elemental mole ratios Si/Al=8.58, Na/Al=0.15, N/Al=1.08, and C/N=4.22.

TABLE 3

| 2-θ | d (Å) | I/I$_o$ % |
|---|---|---|
| 9.06 | 9.75 | w |
| 12.80 | 6.91 | m |
| 16.82 | 5.27 | w |
| 19.28 | 4.60 | w |
| 21.78 | 4.08 | w |
| 23.69 | 3.75 | w |
| 24.24 | 3.67 | w |
| 26.04 | 3.42 | vs |
| 48.54 | 1.87 | w |

EXAMPLE 4

An aluminosilicate stock solution was prepared in the following manner. Aluminum tri-sec- butoxide (95+%), 25.68 g, was added to 712.73 g ethyltrimethylammonium hydroxide (12.8%) with vigorous stirring. To this mixture, 257.64 g colloidal silica, (Ludox AS-40, 40% SiO$_2$) was added, followed by the addition of 3.94 g distilled water. The reaction mixture was homogenized for ½ hr with a high-speed mechanical stirrer, and then aged in a teflon bottle overnight at 98° C. After aging, elemental analysis indicated that the resulting aluminosilicate stock solution contained 4.93 wt. % Si and 0.30 wt. % Al.

A 34.46 g portion of the aluminosilicate sock solution was weighed into a beaker. In a separate beaker, 0.87 g TMACl and 1.14 g KCl was dissolved in 13.54 g de-ionized H$_2$O. This solution was then added to the aluminosilicate stock solution with vigorous stirring and the resulting mixture homogenized for 20 min. A 26.29 g portion of this mixture was then transferred to a 45 mL Telfon-lined autoclave and digested for 10 days at 150° C. at autogenous pressure. The solid product was isolated by centrifugation, washed with de-ionized water and dried at 95° C.

The product was identified as UZM-15 via powder x-ray diffraction. The diffraction lines characteristic of this product are listed in Table 4. Elemental analyses determined the product composition to consist of the elemental mole ratios Si/Al=11.79, K/Al=0.32, N/Al=1.38, and C/N=4.43.

TABLE 4

| 2-θ | d (Å) | I/I$_o$ % |
|---|---|---|
| 8.72 | 10.13 | m |
| 12.75 | 6.94 | m |
| 16.91 | 5.24 | w |
| 19.34 | 4.59 | m |
| 21.75 | 4.08 | w |
| 23.76 | 3.74 | w |
| 24.28 | 3.66 | m |
| 25.76 | 3.46 | vs |
| 48.70 | 1.87 | w |

EXAMPLE 5

Sodium gallate solution (9.91% Ga, 6.31% Na), 7.75 g, was added to 36.82 g ethyltrimethylammonium hydroxide (12.8%) and mixed vigorously. To this mixture, 24.81 g colloidal silica, (Ludox AS-40, 40% SiO$_2$), was added with continuous stirring. In a separate beaker, 0.62 g TMACl (97%) was dissolved in 2.0 g de-ionized H$_2$O. This solution was then added to the previous reaction mixture. The resulting mixture was homogenized for 30 min. A portion of the final reaction mixture, 23.4 g, was transferred to a 45 mL Teflon-lined autoclave and digested at 150° C. for 14d at autogenous pressure. The product was collected by centrifugation, washed with deionized water and dried at 95° C.

The product was identified as UZM-15 by powder x-ray diffraction analysis. Representative diffraction lines are listed in Table 5. Elemental analysis showed the composition of the product to consist of the elemental mole ratios Si/Ga=14.15, Na/Ga=0.31, N/Ga=1.14, and C/N=4.61.

TABLE 5

| 2-θ | d (Å) | I/I$_o$ % |
|---|---|---|
| 8.70 | 10.16 | m |
| 12.70 | 6.96 | m |
| 16.90 | 5.24 | w |
| 19.32 | 4.59 | w |
| 21.40 | 4.15 | w |
| 23.74 | 3.74 | m |
| 24.26 | 3.67 | w |
| 25.70 | 3.46 | vs |
| 48.78 | 1.87 | w |
| 49.64 | 1.83 | w |

EXAMPLE 6

A volume of 91 microliters of a sodium aluminate solution, Na$_2$Al(OH)$_5$, (23%) was pipetted into a teflon reactor. While mixing on an orbital shaker, 648 µL trimethylbutylammonium hydroxide solution, (25.7%) was added with continuous shaking. To this mixture, 273 µL colloidal silica, (Ludox AS-40, 40% SiO$_2$), was added. Finally, 88 µL of sodium chloride, (9.76% solution) was added, also with continuous shaking. The homogenized reaction mixture was vigorously shaken for an hour and the reactor was inserted into an autoclave which was placed into an oven for 72 hours at 175° C. The resulting product was washed, centrifuged, and dried overnight at 75° C.

The x-ray diffraction pattern indicated the product to be the material designated UZM-15. The diffraction lines characteristic of the product are given in table 6.

TABLE 6

| 2-θ | d (Å) | I/I$_o$ % |
|---|---|---|
| 8.80 | 10.04 | m |
| 12.70 | 6.96 | m |
| 16.81 | 5.27 | w |
| 19.21 | 4.62 | m |
| 22.01 | 4.04 | w |
| 23.80 | 3.74 | m |
| 24.30 | 3.66 | m |
| 25.95 | 3.43 | vs |

EXAMPLE 7

An aluminosilicate stock solution was prepared in the following manner. Aluminum tri-sec- butoxide (95+%), 32.57 g, was added to 265.27 g tetraethylorthosilicate. The mixture was homogenized vigorously with an overhead stirrer. To this mixture, 336.52 g propylethyldimethylammonium hydroxide solution (22.24%) was added, followed by the addition of 115.64 g distilled water. The reaction mixture was homogenized for 40 min with a high-speed mechanical stirrer, and then rotary evaporated to remove the ethanol. The reaction mixture was analyzed, the analysis indicated a silicon content of 7.55 wt. % and 0.76 wt. % Al.

A 55.53 g portion of this aluminosilicate stock solution was weighed into a beaker. In a separate beaker, 0.88 g TMACl and 0.91 g NaCl was dissolved in 12.67 g deionized H$_2$O. This solution was then added to the aluminosilicate stock solution with stirring. The resulting mixture was then homogenized for an additional 30 min. The final reaction mixture was distributed among three 45 mL Teflon-lined autoclaves. The autoclaves were then placed in an oven set at 150° C. and the mixture digested for 10, 14, and 20 days. The solids were collected by centrifugation, washed and dried at 95° C.

The isolated products exhibited an x-ray diffraction pattern with the characteristic lines for the material designated UZM-15. Diffraction lines characteristic of the product are given in table 7. The composition of the isolated product from the 20 day digestion consisted of elemental mole ratios Si/Al=9.48, Na/Al=0.23, N/Al=1.00, and C/N=4.6.

TABLE 7

| 2-θ | d (Å) | I/I$_o$ % |
|---|---|---|
| 8.78 | 10.07 | m |
| 13.02 | 6.79 | m |
| 16.87 | 5.25 | w |
| 19.42 | 4.57 | m |
| 21.69 | 4.09 | w |
| 23.72 | 3.75 | w |
| 24.26 | 3.67 | m |
| 25.88 | 3.44 | vs |
| 48.58 | 1.87 | w |

EXAMPLE 8

Sodium gallate solution (9.91% Ga, 6.31% Na), 108 μL, was pipetted into a teflon reactor. While mixing on an orbital shaker, 651 μL of ethyltrimethylammonium hydroxide solution (12.8%) was added. To this mixture, 341 μL colloidal silica, (Ludox AS-40, 40% SiO$_2$), was added with continuous shaking. The resulting mixture was vigorously homogenized for an additonal 30 min. The teflon reactor was inserted into an autoclave which was then placed in an oven set at 150° C. The mixture was digested for 22 days at autogenous pressure. The resulting solid was collected by centrifugation, washed and dried at 75° C.

The isolated product was identified as UZM-15 based on its x-ray diffraction pattern. Diffraction lines characteristic of the product are given in table 8 below.

TABLE 8

| 2-θ | d (Å) | I/I$_o$ % |
|---|---|---|
| 8.60 | 10.27 | m |
| 12.75 | 6.94 | m |
| 17.00 | 5.21 | m |
| 19.59 | 4.53 | m |
| 21.6 | 4.11 | w |
| 24.00* | 3.70 | m |
| 25.70 | 3.46 | vs |

*broad peak, overlap of two unresolved peaks

EXAMPLE 9

The material prepared in Example 1 above was dealuminated to prepare UZM-15HS. A portion of the Example 1 product was treated with a 5 wt. % HCl solution, employing 2 mL of 5 wt. % HCl per gram product. The slurry was heated to 95° C. and held at that temperature for 1 hr. with stirring. The solid was collected and washed with de-ionized water and the above procedure was repeated. The washed material was dried at 95° C. The material was then calcined by ramping to 450° C. in 3.5 hr. with a 17 hr. dwell at 450° C. in air. The HCl treated and calcined material had a composition in terms of mole ratios Si/Al=13.09, Na/Al=0.01, and N/Al=0.07. The BET surface area was determined to be 372 m$^2$/g and the micropore volume was 0.13 cc/g. The x-ray diffraction pattern showed it to be UZM-15HS (Table 9).

TABLE 9

| 2-θ | d (Å) | I/I$_o$ % |
|---|---|---|
| 9.38 | 9.42 | w |
| 12.88 | 6.87 | m |
| 19.53 | 4.54 | w |
| 21.97 | 4.04 | w |
| 23.94 | 3.71 | w |
| 24.38 | 3.65 | m |
| 26.12 | 3.41 | vs |
| 49.12 | 1.85 | w |

EXAMPLE 10

An aluminosilicate stock solution, 569.7 g, containing ETMAOH, Si and Al with an Si/Al ratio of 15.79 was placed in a container. Separately, a solution was prepared by dissolving 32.41 g TMABr and 50.06 g KBr in 371.06 g deionized water. This solution was added to the aluminosilicate solution with vigorous mixing, yielding a clear solution after 20 minutes of mixing. The resulting mixture was transferred to a Parr 2-liter stirred reactor and the mixture was heated to 150° C. over 2 hr. After 48 hr at 150° C., the reaction mixture was allowed to cool. The product was isolated by filtration, washed with deionized water, and dried.

The product was identified as UZM-15 via powder x-ray diffraction analysis. Representative diffraction lines in the pattern are shown below in Table 10. Elemental analysis showed the material to consist of the elemental mole ratios Si/Al=11.07, K/Al=0.81, Na/Al=0.03, N/Al=1.06 and C/N=4.89. A 75 g portion of the product was ammonium exchanged twice in an ammonium nitrate solution (75 g NH$_4$NO$_3$ dissolved in 750 g deionized water) for 2 hr at 80° C. This ammonium exchanged version of the UZM-15 was used for several of the modifications below. A 50 g portion of this product was calcined via a 1° C./min ramp to 500° C. in N$_2$, held at 500° C. for 2 hr before switching the atmosphere to air and held at 500° C. for another 6 hr. Elemental analyses showed the calcined, exchanged UZM-15 product to contain the elemental mole ratios Si/Al=11.07, K/Al=0.01, and Na/Al=0.003. The BET surface area determined by nitrogen adsorption measurements was 361 m$^2$/g and the micropore volume was 0.09 cc/g.

TABLE 10

| 2-θ | d (Å) | I/I$_o$ % |
|---|---|---|
| 7.99* | 11.06 | w |
| 8.98 | 9.84 | w |
| 12.63 | 7.00 | w |
| 13.30* | 6.65 | w |
| 16.95 | 5.23 | w |
| 19.47 | 4.56 | w |
| 20.96 | 4.23 | w |
| 23.82 | 3.73 | w |
| 24.34 | 3.65 | m |

TABLE 10-continued

| 2–θ | d (Å) | I/I₀ % |
|---|---|---|
| 25.90 | 3.44 | vs |
| 48.88 | 1.86 | w |
| 49.68 | 1.83 | w |

*impurity peaks

EXAMPLE 11

A dealumination was carried out via ammonium hexafluorosilicate (AFS) treatment. An AFS solution was prepared by dissolving 1.47 g $(NH_4)_2SiF_6$ in 150 g deionized water. Separately, a zeolite slurry was prepared by suspending 14 g of the ammonium exchanged UZM-15 from Example 10 in 200 g deionized water. The slurry was then added to the AFS solution with mixing. The suspension was stirred for 20 minutes before the reaction mixture was transferred to a teflon bottle, sealed and placed in a shaker bath at 90° C. for 17 hr. The product was isolated by filtration, washed with deionized water, and dried in air.

The dealuminated product of the AFS treatment was identified as UZM-15HS via x-ray powder diffraction analysis, the pattern was very similar to that of the parent UZM-15 material. Representative diffraction lines are shown in Table 11 below. A 12.55 g portion of the AFS product was calcined by ramping the material to 500° C. at 1° C./min in a nitrogen atmosphere, holding at 500° C. for 2 hr in nitrogen and an additional 6 hr in air. The x-ray diffraction pattern for the calcined material is also given in Table 11. Slight shifts and some broadening are observed in some of the diffraction lines as further dealumination of the zeolite framework occurs. Elemental analyses of the calcined product yielded an elemental mole ratio of Si/Al= 13.57, showing that 18% of the Al had been removed from the parent material. Nitrogen adsorption studies showed the BET surface area to be 356 m²/g, while the micropore volume was 0.09 cc/g.

TABLE 11

| AFS UZM-15 | | | Calcined AFS UZM-15 | | |
|---|---|---|---|---|---|
| 2–θ | d (Å) | I/I₀ % | 2–θ | d (Å) | I/I₀ % |
| 7.98* | 11.075 | w | 9.06 | 9.75 | w |
| 8.92(sh) | 9.91 | w | 13.00 | 6.80 | vs |
| 12.92 | 6.85 | m | 19.80 | 4.48 | w |
| 16.98 | 5.22 | w | 24.27 | 3.66 | w |
| 19.33 | 4.59 | w | 24.68 | 3.60 | m |
| 21.86 | 4.06 | w | 26.02 | 3.42 | vs |
| 23.81 | 3.73 | w | | | |
| 24.32 | 3.66 | m | | | |
| 25.86 | 3.44 | vs | | | |
| 48.72 | 1.87 | w | | | |
| 49.77 | 1.83 | w | | | |

*impurity peak,
sh—shoulder

EXAMPLE 12

A dealumination was carried out via oxalic acid (OA) treatments. A 250 ml solution of oxalic acid was prepared using 65 g oxalic acid dihydrate and deionized water. A 30 g portion of the calcined ammonium exchanged UZM-15 from example 10 was added to the solution and the resulting suspension was heated at 71° C. for 2 hr with stirring. The product was isolated by filtration, washed with deionized water and dried at 150° C.

The product was identified as UZM-15HS by powder x-ray diffraction. Representative diffraction lines are given in Table 12 below. A portion of the sample was calcined in air by ramping to 375° C. at 2° C./min and holding at 375° C. for 3 hr. The x-ray diffraction pattern of the calcined material was similar to the treated product and representative diffraction lines are also given in Table 12. Elemental analyses showed the calcined material to consist of the elemental mole ratios Si/Al=15.88, K/Al=0.02, and Na/Al=0.007. The extent of dealumination is such that this material contains 28% less Al than the parent material from example 10. Nitrogen adsorption analysis gave a BET surface area of 340 m²/g and a micropore volume of 0.093 cc/g.

TABLE 12

| OA UZM-15HS | | | OA UZM-15HS (calcined) | | |
|---|---|---|---|---|---|
| 2–θ | d (Å) | I/I₀ % | 2–θ | d (Å) | I/I₀ % |
| 9.401 | 9.39 | w | 9.29 | 9.52 | w |
| 13.00 | 6.80 | vs | 13.16 | 6.72 | vs |
| 19.87 | 4.46 | w | 19.83 | 4.47 | w |
| 24.16 | 3.68 | m | 24.14 | 3.68 | w |
| 24.53 | 3.63 | m | 24.82 | 3.58 | m |
| 26.11 | 3.41 | vs | 26.26 | 3.39 | m |
| 49.38 | 1.84 | w | | | |

EXAMPLE 13

A dealumination was carried out via treatment with hydrochloric acid. A 60 g sample of the parent zeolite from example 10 was slurried in 120 ml of 1.57 M HCl. The slurry was held at 95° C. for 1 hr. The product was isolated by filtration of the hot slurry, and washed thoroughly with deionized water. This process was repeated again, and the product was dried at 95° C. The product was then calcined in nitrogen, ramping to 500° C. at 1° C./min, holding 500° C. for 2 hr in nitrogen and for another 6 hr in air.

The product was identified as UZM-15HS by powder x-ray diffraction analysis. Representative diffraction lines are given in Table 13. Elemental analysis showed the product to contain the elemental mole ratios Si/Al=13.21, K/Al= 0.03, and Na/Al=0.003. This dealumination resulted in the removal of 15% of the aluminum from the zeolite. Nitrogen adsorption measurements showed that the zeolite had a BET surface area of 329 m²/g and a micropore volume of 0.084 cc/g.

TABLE 13

| 2–θ | d (Å) | I/I₀ % |
|---|---|---|
| 9.78 | 9.04 | m |
| 13.00 | 6.81 | vs |
| 19.83 | 4.47 | w |
| 24.06 | 3.70 | m |
| 24.58 | 3.62 | w |
| 26.00 | 3.42 | m |

EXAMPLE 14

An aluminosilicate stock solution was prepared by adding 25.68 g of Aluminum tri sec-butoxide (97+%) to 712.73 g ETMAOH (12.3%) with vigorous stirring, followed by the addition 257.64 g Ludox AS-40 (40% $SiO_2$). The mixture was homogenized for 30 minutes with a high-speed stirrer. The mixture was digested at 98° C. for 36 hours at autogenous pressures. The resulting clear solution was then cooled to room temperature. A second solution was prepared by dissolving 50.06 g of KBr and 32.41 grams of TMABr in 371.60 g of deionized water. It was then added to the entire aluminosilicate solution and mixed for 30 minutes with a high-speed stirrer. The mixture was transferred to an autoclave and crystallized at 150° C. for 6 days at autogenous pressures. The UZM-15 product was isolated by filtration, washed with deionized water, and dried at 70° C. The material was then slurried in a 1.57M aqueous HCl solution for 1 hour at 95° C., filtered and washed. This procedure was repeated 2 times. The material was then washed and dried at 95° C.

The acid extracted product was identified as UZM-15HS by powder x-ray diffraction analysis. Representative diffraction lines for the product are listed in Table 14. Elemental analysis showed the product to consist of the elemental mole ratio Si/Al=14.25. The BET surface area of the calcined material determined by nitrogen adsorption was 380 m²/g and the micropore volume was 0.11 cc/g.

Further dealumination of the above sample was carried out by steaming 60 g of the sample at 600° C. for 4 hrs with 50% steam using a horizontal steamer. Nitrogen adsorption showed the BET surface area of the steamed sample to be 275 m²/g, while the micropore volume is 0.063 cc/g. A 20 g portion of the steamed UZM-15HS was acid extracted using a solution prepared by diluting 19.7 g HNO$_3$ (69%) in 350 g de-ionized water. The solution was heated to 90° C. before the addition of the steamed UZM-15HS. The resulting slurry was stirred for 1 hr at 90° C. The product was isolated by filtration, washed with de-ionized water, and dried at 98° C. The modified product was determined to be UZM-15HS via x-ray powder diffraction analysis. Characteristic diffraction lines for the product are listed in Table 14. Elemental analyses showed the product to have the elemental mole ratio Si/Al=20.1.

TABLE 14

| Acid extracted UZM-15 (UZM-15HS) | | | Acid-Steam-Acid UZM-15 (UZM-15HS) | | |
|---|---|---|---|---|---|
| 2–θ | d (Å) | I/I$_o$ % | 2–θ | d (Å) | I/I$_o$ % |
| 9.58 | 9.23 | w | 9.86 | 8.96 | w |
| 12.98 | 6.81 | vs | 13.19 | 6.70 | vs |
| 19.73 | 4.50 | w | 19.97 | 4.44 | w |
| 24.00 | 3.70 | m | 26.24 | 3.39 | vs |
| 24.48 | 3.63 | w | | | |
| 25.96 | 3.43 | s | | | |

We claim as our invention:

1. A microporous crystalline zeolite having a composition in the as-synthesized and anhydrous form in terms of mole ratios of the elements of:

$$M_m^{n+}R_r^{p+}Al_{(1-x)}E_xSi_yO_z$$

where M is at least one exchangeable cation selected from the group consisting of alkali and alkaline earth metals, "m" is the mole ratio of M to (Al+E) and varies from 0 to about 2.0, R is at least one first quaternary organoammonium cation comprising at least one organic group having at least 2 carbon atoms, and optionally a second organoammonium cation selected from the group consisting of quaternary ammonium cations, protonated amines, protonated diamines, protonated alkanolamines, diquaternaryammonium cations, quaternized alkanolamines and mixtures thereof, "r" is the mole ratio of R to (Al+E) and has a value of about 0.25 to about 5.0, E is an element selected from the group consisting of Ga, Fe, In, Cr, B, and mixtures thereof, "x" is the mole fraction of E and varies from 0 to 1.0, "n" is the weighted average valence of M and has a value of about +1 to about +2, "p" is the weighted average valence of R and has a value of +1 to about +2, "y" is the mole ratio of Si to (Al+E) and varies from about 7 to about 50 and "z" is the mole ratio of O to (Al+E) and has a value determined by the equation:

$$z=(m·n+r·p+3+4·y)/2;$$

the zeolite characterized in that it has an x-ray diffraction pattern having at least the d-spacings and relative intensities set forth in Table A

TABLE A

| 2–θ | d (Å) | I/I$_o$ % |
|---|---|---|
| 8.35–9.30 | 10.58–9.75 | w–m |
| 12.30–13.30 | 7.19–6.65 | w–m |
| 16.60–17.20 | 5.34–5.15 | w–m |
| 19.00–19.80 | 4.67–4.48 | w–m |
| 20.80–22.30 | 4.27–3.98 | w |
| 23.55–23.95 | 3.77–3.71 | w–m |
| 24.03–24.47 | 3.70–3.63 | w–m |
| 25.50–26.25 | 3.49–3.39 | vs |
| 48.30–49.10 | 1.88–1.85 | w. |

2. The zeolite of claim 1 where M is selected from the group consisting of sodium, potassium, lithium, strontium, barium and mixtures thereof.

3. The zeolite of claim 1 where "m" is zero.

4. The zeolite of claim 3 where R is only a first organoammonium cation selected from the group consisting of diethyldimethylammonium, ethyltrimethylammonium, trimethylbutylammonium, propylethyldimethylammonium N,N,N'N',N',N'-hexamethyl-1,4 butanediammonium cations and mixtures thereof.

5. The zeolite of claim 1 where R is a mixture of a first organoammonium cation selected from the group consisting of diethyldimethylammonium, ethyltrimethylammonium, trimethylbutylammonium, propylethyldimethylammonium N,N,N,N',N',N'-hexamethyl-1,4 butanediammonium cations and mixtures thereof and a quaternary ammonium cation.

6. The zeolite of claim 1 where the second organoammonium cation is a quaternary ammonium cation selected from the group consisting of tetramethylammonium, propyltrimethylammonium, hexamethonium, N,N, N,N',N', N' hexamethyl-1,4 butanediammonium, and mixtures thereof.

7. A process for preparing a microporous crystalline zeolite having a composition in the as-synthesized and anhydrous form in terms of mole ratios of the elements given by $$M_m^{n+}R_r^{p+}Al_{(1-x)}E_xSi_yO_z$$

where M is at least one exchangeable cation selected from the group consisting of alkali and alkaline earth metals, "m" is the mole ratio of M to (Al+E) and varies from 0 to about 2.0, R is at least one first quaternary organoanimonium cation comprising at least one organic group having at least two carbon atoms, and optionally a second organoammonium cation selected from the group consisting of quaternary ammonium cations, protonated amines, protonated diamines, protonated alkanolamines, diquaternaryammonium cations, quaternized alkanolamines and mixtures thereof, "r" is the mole ratio of R to (Al+E) and has a value of about 0.25 to about 5.0, E is an element selected from the group consisting of Ga, Fe, In, Cr, B, and mixtures thereof "x" is the mole fraction of E and varies from 0 to 1.0, "n" is the weighted avenge valence of M and has a value of about +1 to about +2, "p" is the weighted average valence of R and has a value of +1 to about +2, "y" is the mole ratio of Si to (Al+2) and varies from about 7 to about 50 and "z" is the mole ratio of O to (Al+E) and has a value determined by the equation:

$$z=(m \cdot n + r \cdot p + 3 + 4 \cdot y)/2;$$

the zeolite characterized in that it has an x-ray diffraction pattern having at least the d-spacings and relative intensities set forth in Table A

TABLE A

| 2-θ | d (Å) | I/I$_o$ % |
|---|---|---|
| 8.35–9.30 | 10.58–9.75 | w–m |
| 12.30–13.30 | 7.19–6.65 | w–m |
| 16.60–17.20 | 5.34–5.15 | w–m |
| 19.00–19.80 | 4.67–4.48 | w–m |
| 20.80–22.30 | 4.27–3.98 | w |
| 23.55–23.95 | 3.77–3.71 | w–m |
| 24.03–24.47 | 3.70–3.63 | w–m |
| 25.50–26.25 | 3.49–3.39 | vs |
| 48.3–49.10 | 1.88–1.85 | w | the process comprising forming a reaction mixture containing reactive sources of R, Al, Si and optionally E and/or M and heating the reaction mixture at a temperature of about 85° C. to about 225° C., the reaction mixture having a composition expressed in terms of mole ratios of the oxides of:

$$aM_{2/n}O:bR_{2/p}O:(1-c)Al_2O_3:cE_2O_3:dSiO_2:eH_2O$$

where "a" has a value of 0 to about 5.0, "b" has a value of about 1.5 to about 80, "c" has a value of 0 to about 1.0, "d" has a value of 10 to about 100, and "e" has a value of about 100 to about 15000.

8. The process of claim 7 where M is selected from the group consisting of potassium, lithium, sodium, cesium, strontium, barium and mixtures thereof.

9. The process of claim 7 where the source of M is selected from the group consisting of halide, nitrate, sulfate, hydroxide, or acetate compounds.

10. The process of claim 7 where the first organoammonium cation is selected from the group consisting of diethyldimethylammonium, ethyltrimethylammonium, trimethylbutylammonium, propylethyldimethylammonium, N,N,N,N',N',N' hexamethyl-1,4 butanediammonium cations and mixtures thereof.

11. The process of claim 7 where the second organoammonium cation is a quaternary ammonium cation selected from the group consisting of tetramethylammonium, hexamethonium, propyltrimethylammonium, N,N,N,N',N', N' hexamethyl-1,4 butanediammonium, and mixtures thereof.

12. The process of claim 7 where the source of R is the halide or hydroxide compounds of R.

13. The process of claim 7 where the aluminum source is selected from the group consisting of aluminum isopropoxide, aluminum sec-butoxide, precipitated alumina and aluminum metal.

14. The process of claim 7 where the silicon source is selected from the group consisting of tetraethylorthosilicate, colloidal silica, fumed silica and precipitated silica.

15. The process of claim 7 where the E source is selected from the group consisting of alkali borates, boric acid, gallium oxyhydroxide, gallium sulfate, ferric sulfate, ferric chloride, chromium nitrate, indium chloride and mixtures thereof.

16. The process of claim 7 where the source of R, aluminum, and silicon comprises an organoammonium aluminosilicate solution.

17. A hydrocarbon conversion process comprising contacting a hydrocarbon with a catalytic composite at hydrocarbon conversion conditions to give a converted product, the catalytic composite comprising a microporous crystalline zeolite selected from the group consisting of UZM-15, UZM-15HS and mixtures thereof wherein UZM-15 has a composition in the as-synthesized and anhydrous form in terms of mole ratios of the elements given by $$M_m^{n+}R_r^{p+}Al_{(1-x)}E_xSi_yO_z$$

where M is at least one exchangeable cation selected from the group consisting of alkali and alkaline earth metals, "in" is the mole ratio of M to (Al+E) and varies from 0 to about 2.0, R is at least one first quaternary organoammonium cation comprising at least one organic group having at least two carbon atoms, and optionally a second organoammonium cation selected from the group consisting of quaternary ammonium cations, protonated amines, protonated diamines, protonated alkanolamines, diquaternaryammonium cations, quaternized alkanolamines and mixtures thereof, "r" is the mole ratio of R to (Al+E) and has a value of about 0.25 to about 5.0, E is an element selected from the group consisting of Ga, Fe, In, Cr, B, and mixtures thereof "x" is the mole fraction of E and varies from 0 to 1.0, "n" is the weighted average valence of M and has a value of about +1 to about +2, "p" is the weighted average valence of R and has a value of +1 to about +2, "y" is the mole ratio of Si to (Al+E) and varies from about 7 to about 50 and "z" is the mole ratio of O to (Al+E) and has a value determined by the equation:

$$z=(m \cdot n + r \cdot p + 3 + 4 \cdot y)/2;$$

the zeolite characterized in that it has an x-ray diffraction pattern having at least the d-spacings and relative intensities set forth in Table A

TABLE A

| 2-θ | d (Å) | I/I$_o$ % |
|---|---|---|
| 8.35–9.30 | 10.58–9.75 | w–m |
| 12.30–13.30 | 7.19–6.65 | w–m |
| 16.60–17.20 | 5.34–5.15 | w–m |
| 19.00–19.80 | 4.67–4.48 | w–m |
| 20.80–22.30 | 4.27–3.98 | w |
| 23.55–23.95 | 3.77–3.71 | w–m |
| 24.03–24.47 | 3.70–3.63 | w–m |
| 25.50–26.25 | 3.49–3.39 | vs |
| 48.30–49.10 | 1.88–1.85 | w | and UZM-15HS has an empirical composition on an anhydrous basis in terms of mole ratios of the elements of:

$$M1_a^{n+}Al_{(1-x)}E_xSi_yO_z$$

where M1 is at least one exchangeable cation selected from the group consisting of alkali metals, alkaline earth metals, rare earth metals, ammonium ion, hydrogen ion and mixtures thereof, a is the mole ratio of M1 to (Al+E) and varies from about 0.01 to about 50, E is an element selected from the group consisting of gallium, iron, boron, chromium, indium and mixtures thereof, x is the mole fraction of E and varies from 0 to about 1.0, n is the weighted average valence of M1 and has a value of about +1 to about +3, y' is the mole ratio of Si to (Al+E) and is greater than about 7 and z" is the mole ratio of O to (Al+E) and has a value determined by the equation:

$$z''=(a \cdot n + 3 + 4 \cdot y')/2;$$

the zeolite characterized in that it has at least the diffraction lines listed in Table B

TABLE B

| 2-θ | d (Å) | I/I₀ % |
|---|---|---|
| 8.75–10.30 | 10.12–8.60 | w–vs |
| 12.70–13.40 | 6.98–6.62 | m–s |
| 19.00–20.30 | 4.68–4.38 | w |
| 25.50–26.50 | 3.50–3.37 | m–vs | the UZM-15HS characterized in that it is derived from UZM-15.

18. A microporous crystalline zeolite UZM-15HS having an empirical composition on an anhydrous basis in terms of mole ratios of the elements of:

$$M1_a^{n+}Al_{(1-x)}E_xSi_yO_{z''}$$

where M1 is at least one exchangeable cation selected from the group consisting of alkali metals, alkaline earth metals, rare earth metals, ammonium ion, hydrogen ion and mixtures thereof, a is the mole ratio of M1 to (Al+E) and varies from 0.01 to about 50, E is an element selected from the group consisting of gallium, iron, boron, chromium, indium and mixtures thereof; x is the mole fraction of E and varies from 0 to about 1.0, n is the weighted average valence of M1 and has a value of about +1 to about +3, y' is the mole ratio of Si to (Al+E) and is greater than about 7 and z'' is the mole ratio of O to (Al+E) and has a value determined by the equation:

$$z''=(a \cdot n+3+4 \cdot y')/2;$$

the zeolite characterized in that it has an x-ray diffraction pattern having at least the d-spacings and relative intensities set forth in Table B

TABLE B

| 2-θ | d (Å) | I/I₀ % |
|---|---|---|
| 8.75–10.30 | 10.12–8.60 | w–vs |
| 12.70–13.40 | 6.98–6.62 | m–s |
| 19.00–20.30 | 4.68–4.38 | w |
| 25.50–26.50 | 3.50–3.37 | m–vs | the UZM-15HS characterized in that it is derived from UZM-15.

19. The zeolite of claim 18 where M1 is selected from the group consisting of lithium, cesium, sodium, potassium, strontium, barium, calcium, magnesium, lanthanum, hydrogen ion, ammonium ion and mixtures thereof.

20. The zeolite of claim 18 where M1 is a hydrogen ion.

21. The zeolite of claim 18 where y' has a value from about 7 to about 20,000.

22. The zeolite of claim 18 where y' has a value from about 7 to about 3,000.

23. A process for preparing a modified microporous crystalline zeolite having an empirical composition on an anhydrous basis in terms of mole ratios of the elements of:

$$M1_a^{n+}Al_{(1-x)}E_xSi_yO_z$$

where M1 is at least one exchangeable cation selected from the group consisting of alkali metals, alkaline earth metals, rare earth metals, ammonium ion, hydrogen ion and mixtures thereof, a is the mole ratio of M1 to (Al+E) and varies from about 0.01 to about 50, E is an element selected from the group consisting of gallium, iron, boron, chromium, indium and mixtures thereof, x is the mole fraction of E and varies from 0 to about 1.0, n is the weighted average valence of M1 and has a value of about +1 to about 3, y' is the mole ratio of Si to (Al+E) and is greater than about 7 and z'' is the mole ratio of O to (Al+E) and has a value determined by the equation:

$$z''=(a \cdot n+3+4 \cdot y')/2$$

the zeolite characterized in that it has an x-ray diffraction pattern having at least the d-spacings and relative intensities of Table B,

TABLE B

| 2-θ | d (Å) | I/I₀ % |
|---|---|---|
| 8.75–10.30 | 10.12–8.60 | w–vs |
| 12.70–13.40 | 6.98–6.62 | m–s |
| 19.00–20.30 | 4.68–4.38 | w |
| 25.50–26.50 | 3.50–3.37 | m–vs | the process comprising treating a starting zeolite at treating conditions thereby removing at least a portion of the framework aluminum and optionally inserting silicon into the framework to provide the modified zeolite; the starting zeolite having an empirical formula on an anhydrous basis of:

$$M_{m'}^{n+}R_{r'}^{p+}Al_{(1-x)}E_xSi_yO_{z'}$$

where M' is an exchangeable cation selected from the group consisting of ammonium ion, hydrogen ion, alkali metals, alkaline earth metals, rare earth metals and mixtures thereof; n is the weighted average valence of M' and varies from +1 to about +3, m' is the mole ratio of M' to (Al+E) and varies from 0 to about 7.0, R is at least one first quaternary organoammonium cation comprising at least one organic group having at least 2 carbon atoms and optionally a second organoammonium cation selected from the group consisting of protonated amines, protonated diamines, protonated alkanolamines, quaternary ammonium ions, diquarternary ammonium ions, quaternized alkanolammonium ions and mixtures thereof, p is the average weighted valence of the organic cation and varies from about +1 to about +2, r' is the mole ratio of R to (Al+E) and varies from 0 to about 7.0, r'+m'>0, y' is the ratio of Si to (Al+E) and varies from about 7 to 50 and z' is the mole ratio of O to (Al+E) and has a value given by the equation:

$$z'=(m' \cdot n+r' \cdot p+3+4 \cdot y')/2.$$

the zeolite characterized in that it has an x-ray diffraction pattern having at least the d-spacings and relative intensities set forth in Table A

TABLE A

| 2-θ | d (Å) | I/I₀ % |
|---|---|---|
| 8.35–9.30 | 10.58–9.75 | w–m |
| 12.30–13.30 | 7.19–6.65 | w–m |
| 16.60–17.20 | 5.34–5.15 | w–m |
| 19.00–19.80 | 4.67–4.48 | w–m |
| 20.80–22.30 | 4.27–3.98 | w |
| 23.55–23.95 | 3.77–3.71 | w–m |
| 24.03–24.47 | 3.70–3.63 | w–m |
| 25.50–26.25 | 3.49–3.39 | vs |
| 48.30–49.10 | 1.88–1.85 | w. |

* * * * *